US006277417B1

(12) United States Patent
Anderson

(10) Patent No.: US 6,277,417 B1
(45) Date of Patent: Aug. 21, 2001

(54) METHOD OF INHIBITING 5α-REDUCTASE WITH ASTAXANTHIN

(75) Inventor: Mark Anderson, Carmel, NY (US)

(73) Assignee: Triarco Industries, Inc., Wayne, NJ (US)

( * ) Notice: Subject to any disclaimer, the term of this patent is extended or adjusted under 35 U.S.C. 154(b) by 0 days.

(21) Appl. No.: 09/546,316

(22) Filed: Apr. 7, 2000

(51) Int. Cl.$^7$ ............................ A61K 35/78; C12P 23/00; C07C 403/00
(52) U.S. Cl. ............................ 424/727; 435/67; 435/183; 435/189; 514/691; 514/724; 585/351
(58) Field of Search .................................. 424/195.1, 727; 435/183, 189, 67; 585/351; 514/691, 724

(56) References Cited

U.S. PATENT DOCUMENTS

| | | | |
|---|---|---|---|
| 5,705,180 | * | 1/1998 | Schlipalius .............................. 424/423 |
| 5,858,700 | * | 1/1999 | Ausich et al. ........................... 435/67 |
| 5,972,985 | * | 10/1999 | Thomas et al. ........................ 514/400 |

OTHER PUBLICATIONS

Tanaka et al. Cancer Res. vol. 55, No. 18, pp. 4059–4064, CANCERLIT abstract enclosed, 1995.*
Bendich, A. et al. "Biological actions of carotenoids", FASEP J., vol. 3, pp. 1927–1932 (1989).
Bendich, A. et al. "Carotenoids and the immune response", J. Nutr., vol. 119, pp. 112–115 (1989).
Ziegler, R.G. "A review of epidemiologic evidence that carotenoids reduce the risk of cancer", J. Nutr., vol. 119, pp. 116–122 (1989).
Braekman, J., Curr. Ther. Res., vol. 55, pp. 776–785 (1994).
Casarosa, C. et al., Clin. Ther., vol. 10, pp. 585–588 (1988).
Bennet, B. C. and Hicklin, J. R., Economic Botony, vol. 52(4), pp. 381–393 (1998).
Bone, K., The European Journal of Herbal Medicine, vol. 4(1), pp. 15–24 (1998).
Bonnet, P. et al., J. Clin. Endocr. Metab., vol. 77, pp. 1203–1208 (1993).
Brinkmann, A.O. et al., J. Steroid Biochem. Mol. Biol., vol. 41, p. 361 (1992).
Chaudry, A. A. et al., Int. J. Cancer, vol. 57, pp. 176–180 (1994).
Clinton, Nutr. Rev., vol. 56(2), pp. 35–51 (1998).
Cooper et al., J. Chem Soc. Perkins Trans. I, (1975) pp. 2195–2204.
Délos, S. et al., Journal of Steroid Biochemistry and Molecular Biology, vol. 48, pp. 347–352 (1994).

Di Silverio, F. et al., Eur. Urol., vol. 21, pp. 309–314 (1992).
Gerster, H. J. Amer. Coll. Nutr., vol. 16, pp. 109–126 (1997).
Hirsh, K.S. et al., Proc. Natl. Acad. Sci. USA, vol. 90, pp. 5277–5281 (1990).
Iehlé, C. et al., Journal of Steroid Biochemistry and Molecular Biology, vol. 54, pp. 273–279 (1995).
Isaacs, J.T. et al., J. Androl., vol. 13, pp. 457–464 (1992).
Lorenz, R.T. "A Technical Review of NatuRose™ Haemoatococcus algae meal.", Cyanotech Corp. Technical Bulletin #058 (Jan. 20, 1999).
Lowe, F. C. et al., Urology, vol. 48(1), pp. 12–20 (1996).
Paubert–Braquet, M. et al., Pharmacol. Res., vol. 34, pp. 171–179 (1996).
Paubert–Braquet, M. et al., Prostaglandins Leukot, Essent. Fatty Acids, vol. 57, pp. 299–304 (1997).
Paubert–Braquet, M. et al., Eur. Urol., vol. 33, pp. 340–347 (1998).
Rao, V.A. and Agarwal, S., Nutrition Research, vol. 19(2), pp. 305–323 (1999).
Rhodes, L. et al., Prostate, vol. 22, pp. 43–51 (1993).
Seybold and Goodwin, Nature, vol. 184, pp. 1714–1715 (1959).
Simental, J.A. et al., J. Steroid Biochem. Mol. Biol., vol. 43, p. 37 (1992).
Stahl, W. and Sies, H., Arch. Biochem. Biophys., vol. 336, pp. 1–9 (1996).
Steiner, M.S., Urology, vol. 42, pp. 99–110 (1993).
Strauch, G. et al., Eur. Urol., vol. 26, pp. 247–252 (1994).
Sultan, C. et al., J. Steroid Biochem., vol. 20, pp. 515–519 (1984).
Taylor, E. W. et al., Pharm. Res., vol. 14, pp. 572–577 (1997).
Tyler, V.E., The Honest Herbal: A sensible guide to the use of herbs and related remedies. (Pharmaceutical Products Press, New York 1982).
Tyler, V.E., Herbs of Choice: The therapeutic use of phytochemicals. (Pharmaceutical Products Press, New York 1994) pp. 81–82.
Ware, L.J. et al., Cancer Metastasis Rev., vol. 12, pp. 287–301 (1993).
Yee, S., Pharm. Res., vol. 14, pp. 763–766 (1997).

* cited by examiner

Primary Examiner—Christopher R. Tate
(74) Attorney, Agent, or Firm—Fitzpatrick, Cella, Harper & Scinto

(57) ABSTRACT

A method for inhibiting the activity of the enzyme 5α-reductase in a human subject is provided which comprises administering to the subject a composition comprising the carotenoid astaxanthin. Administration of the composition to inhibit the enzyme is useful to prevent and treat benign prostate hyperplasia (BPH) and prostate cancer in human males.

9 Claims, No Drawings

METHOD OF INHIBITING 5α-REDUCTASE WITH ASTAXANTHIN

FIELD OF THE INVENTION

This invention relates to methods of inhibiting the activity of the enzyme 5α-reductase. More particularly, this invention relates to methods of inhibiting 5α-reductase by administration of a composition comprising the carotenoid astaxanthin, derivable from *Haematococcus pluvialis* microalgae, to treat or prevent disorders in humans resulting from the activity of the enzyme, in particular benign prostate hyperplasia and prostate cancer.

BACKGROUND OF THE INVENTION

Enlargement of the prostate, which affects fifty percent of men aged 60 and ninety percent of men by age 85, is commonly referred to as benign prostate hyperplasia (BHP).

BPH is a slow, progressive enlargement of the fibromuscular and epithelial structures of the prostate gland. The symptoms of BPH include decreased urinary flow, urinary retention, frequent urination and impotency. Substantial evidence indicates that the androgens testosterone and dihydrotestosterone (DHT) are contributing factors in producing BPH in the prostate. Tyler, V. E., *The Honest Herbal: A sensible guide to the use of herbs and related remedies*. (Pharmaceutical Products Press, New York 1982). Testosterone is converted by 5α-reductase to DHT which is about five times more potent than testosterone. DHT binds to cytoplasmic receptors in the prostate, where it initiates RNA and DNA synthesis. This action, in turn induces protein synthesis and abnormal growth of the prostate. (Tyler, V. E., *Herbs of Choice: The therapeutic use of phytochemicals*. (Pharmaceutical Products Press, New York 1994)). Current clinical evidence indicates that inhibition of 5α-reductase reverses the symptoms of BPH in human males. (Strauch, G. et al., *Eur. Urol.*, Vol. 26, pp. 247–252 (1994); Rhodes, L. et al., *Prostate*, Vol. 22, pp. 43–51 (1993)).

There is now substantial evidence that androgen deprivation can decrease the obstructive symptoms of BPH. Further, 5α-reductase activity appears to be higher in cells obtained from BPH tissue than from normal prostate tissue. (Bone, K., The European Journal of Herbal Medicine, Vol. 4(1), pp. 15–24 (1998)). Inhibitors of 5α-reductase, such as the drug finasteride (PROSCAR), block the conversion of testosterone to DHT and have been found to reduce the size of the prostate leading to an increase in peak urinary flow rate and a reduction in symptoms (Strauch et al. 1994; Rhodes et al. 1993). Natural products such as the lipid extracts of Saw Palmetto berries (LESP), *Serenoa repens*, have also been found to reduce the conversion of testosterone to DHT by the inhibition of 5α-reductase both in vitro and in vivo (Bone, 1998; Di Silverio, F. et al., *Eur. Urol.*, Vol. 21, pp. 309–314 (1992)).

Further, 5α-reductase has also been implicated as playing a central role in the proliferation of prostate cancer. Iehlé, C. et al., *Journal of Steroid Biochemistry and Molecular Biology*, Vol. 54, pp. 273–279 (1995) (and references cited therein). See also, Isaacs, J. T. et al., *J. Androl.*, Vol. 13 p. 457 (1992); Brinkmann, A. O. et al., *J. Steroid Biochem. Mol. Biol.*, Vol. 41, p. 361 (1992); Simental, J. A. et al., *J. Steroid Biochem. Mol. Biol.*, Vol. 43, p. 37 (1992); Ware, L. J. et al., *Cancer Metastasis Rev.*, Vol. 12, p. 287 (1993); Steiner, M. S., *Urology*, Vol. 42, p. 99 (1993).

Astaxanthin, a red carotenoid has the following structure:

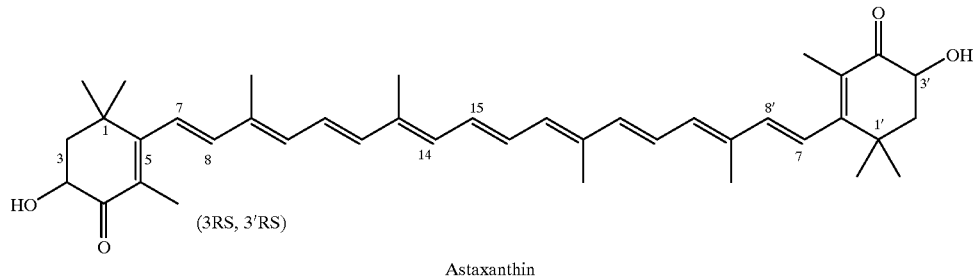

Astaxanthin

*Haematococcus pluvialis* microalgae is a natural source of astaxanthin. The microalgae also contains fatty acids such as palmitic, oleic, linoleic and stearic acids, protein, minerals, carbohydrates and vitamins. As explained more fully below, the present invention comprises the discovery that when tested in a 5α-reductase in vitro assay with a pre-digestion model, *Haematococcus pluvialis* algae meal containing the carotenoid astaxanthin demonstrated 98% inhibition of 5α-reductase at a concentration of 300 μg/mL.

Thus, the major advantage provided by the present invention is a method of inhibiting the enzyme 5α-reductase in a human subject by the administration of a composition comprising the carotenoid astaxanthin. Because of its ability to inhibit the enzyme 5α-reductase, a composition comprising the carotenoid astaxanthin would therefore be useful for preventing and/or treating Benign Prostate Hyperplasia in a human subject, and preventing and/or treating prostate cancer in a human subject by administering a composition comprising astaxanthin to the subject.

These and additional objects and advantages of the present invention are shown from the description below. The disclosures of the publications cited above and throughout this specification are incorporated in their entirety to more fully describe the invention and to demonstrate the state of the art.

SUMMARY OF THE INVENTION

This invention provides a method for inhibiting the activity of the enzyme 5α-reductase in a human subject which comprises administering to the subject a composition comprising the carotenoid astaxanthin.

The invention also provides a method for treating Benign Prostate Hyperplasia in a human subject which comprises administering to the subject a composition comprising the carotenoid astaxanthin.

The invention further provides a method for preventing Benign Prostate Hyperplasia in a human subject which comprises administering to the subject a composition comprising the carotenoid astaxanthin.

The invention further provides a method for treating prostate cancer in a human subject which comprises administering to the subject a composition comprising the carotenoid astaxanthin.

Finally the invention provides a method for preventing prostate cancer in a human subject which comprises administering to the subject a composition comprising the carotenoid astaxanthin.

DETAILS OF THE INVENTION

In the practice of the methods of this invention, astaxanthin is administered to a human subject in need of treatment and/or prevention of ailments caused by the activity of the enzyme 5α-reductase. The enzyme 5α-reductase is known to exist in two distinct isozymes, designated type 1 (displaying maximal activity at neutral-basic pH) and type 2 (displaying maximal activity at acidic pH). There is evidence for the expression of both types in the prostate. Hirsh, K. S. et al., *Proc. Natl. Acad. Sci. USA*, Vol. 90, pp. 5277–5281 (1990); Bonnet, P. et al., *J. Clin. Endocr. Metab.*, Vol. 77, pp. 1203–1208 (1993). As used herein, the term "5α-reductase", and the ability of the compounds described herein to inhibit the activity of the enzyme "5α-reductase", is meant to encompass both type 1 and type 2. Compositions containing astaxanthin are demonstrated herein to inhibit the activity of the enzyme 5α-reductase in in vitro assays that are closely predictive of the ability of such compounds to inhibit the enzyme in a human subject.

In the practice of the methods of this invention astaxanthin from any source, whether natural or synthetic, can be used. Synthetic methods for preparing astaxanthin are known (R. D. G. Cooper et al., *J. Chem Soc. Perkins Trans. I*, (1975) p. 2195; F. Kienzle, H. Mayer, *Helv. Chim. Acta.*, (1978) Vol. 61, p. 2609) as are methods of isolating astaxanthin from natural sources (Tischer, *Z. Physiol. Chem.*, (1941) Vol. 267 p. 281; Seybold and Goodwin, Nature, (1959) Vol. 184, p. 1714). *Haematococcus pluvialis* microalgae is a preferred natural, commercially available source of the astaxanthin used in the methods of this invention. Thus, astaxanthin can be administered in a pure form as synthesized or isolated from natural sources. Alternatively, and as a preferred embodiment of the methods of the invention, astaxanthin is administered as part of a composition comprising protein, carbohydrate, and fatty acids. When *Haemotococcus pluvialis* algae meal is used as the source of astaxanthin, the composition is preferrably administered as derived from the microalgae, comprising the natural protein, carbohydrate, and fatty acid components of the microalgae. Such microalgae is commercially available (Cyanotech Corporation, Kailua-Kona, Hi.) and generally comprises as major components (by weight), from 1.5 to 2% astaxanthin, 15 to 30% protein, 35 to 40% carbohydrates, 10 to 25% ash, 5 to 20% fat, and 3 to 10% moisture. The composition further comprises minor components including iron, magnesium, calcium, biotin, L-carnitine, folic acid, niacin, pantothenic acid, and vitamins B1, B2, B6, B12, C, and E.

Thus, in the practice of the invention, the composition can comprise from about 0.1% to about 75% by weight astaxanthin, from about 0.1% to about 99.9% by weight protein, from about 0.1% to about 99.9% by weight carbohydrate, and from about 0.1% to 99.9% fatty acids. In a particularly preferred embodiment, the composition comprises from about 15% to about 35% by weight protein, from about 15% to about 60% by weight carbohydrates, from about 1% to about 30% by weight fatty acids, and from about 0.1% to about 4.0% by weight of the carotenoid astaxanthin.

The compositions administered in the methods of the invention can further comprise saw palmetto extracts, which are commonly referred to as lipid extracts or liposterolic extracts of saw palmetto (LESP). The use of each of these is synonymous herein. These extracts can be prepared readily by extraction of the dried berries of saw palmetto, *Serenoa repens*, for example with either hexane or ethanol. More recently, extracts prepared using supercritical carbon dioxide have become available. The hexane extract is preferred, due to the fact that it has been the subject of more clinical investigations than the others. However, the extracts produced by other methods are believed to be very similar chemically. LESP typically comprises from about 85% to about 90% free fatty acids and from about 0.2% to about 0.4% total sterols, the majority of which is β-sitosterol.

In a preferred embodiment the compositions administered in the methods of the invention comprise from about 0.1% to about 99.9% by weight *Haematococcus pluvialis* algae meal containing astaxanthin and from about 0.1% to about 99.9% by weight saw palmetto extracts in addition to comprising the carotenoid astaxanthin. In a preferred embodiment, the compositions comprise from about 0.5% to about 50% by weight *Haematococcus pluvialis* algae meal containing astaxanthin and from about 0.1% to about 99.9% by weight saw palmetto extracts.

In the practice of the methods of the invention, the composition may be administered orally in any of the usual solid forms such as pills, tablets, capsules or powders, including sustained release preparations. The term unit dosage form as used in this specification and the claims refer to physically discrete units to be administered in single or multiple dosage to humans, each unit containing a predetermined quantity of active material, i.e., astaxanthin and/or astaxanthin in combination with protein, carbohydrate, and fatty acis, and/or astaxanthin in combination with LESP, any of the above in association with one or more carriers. The quantity of active material is that calculated to produce the desired therapeutic effect upon administration of one or more of such units. Of course, it is understood that the exact treatment level will depend upon the case history of the human subject to be treated. The precise treatment level can be determined by one of ordinary skill in the art without undue experimentation, taking into consideration such factors as age, size, severity of condition, and anticipated duration of administration of compounds, among other factors known to those of ordinary skill.

Unit dosages can range from about 3.0 mg/kg to about 100 mg/kg (the unit designated "mg/kg" as used herein refers to mg of astaxanthin and/or astaxanthin in combination with protein, carbohydrate, and fatty acids and/or astaxanthin in combination with LESP, per kilogram of body weight), preferably from about 10 mg/kg to about 30 mg/kg, most preferably about 20 mg/kg. The doses can be administered in any convenient dosing schedule to achieve the stated beneficial effects. For example, the doses can be taken 1, 2, 3, 4, 5 or more times daily. Preferably 3 doses are taken daily. Most preferably, the doses are taken at meal times. The dosages may be taken orally in any suitable unit dosage form such as pills, tablets, and capsules. Preferred are capsules made from gelatin.

As used herein, the term "carrier" denotes a solid or liquid filler, diluent, or encapsulating substance. Some examples of the substances that can act as carriers are sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils, such as peanut oil, cottonseed oil, sesame oil, olive oil, corn oil and of the broma; polyols such as propylene glycol, glcerin, sorbitol, mannitol, and polyethylene glycol; agar, alginic acid; pyrogen-free water; isotonic saline; ethyl alcohol and phosphate buffer solutions, as well as other non-toxic compatible substances used in preparation of formulations. Wetting agents and lubricants such as sodium lauryl sulfate, as well as coloring agents, flavoring agents, and preservatives can also be present. Dye stuffs or pigments may be added to the tablets, for example, for identification or in order to characterize combinations of active doses.

Other preparations that can be used orally include push-fit capsules made of gelatin, as well as soft, sealed capsules made of gelatin and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Powders are prepared by comminuting the compositions of the present invention to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added improve the availability of the medicament when the capsule is ingested.

Tablets are made by preparing a powder mixture, granulating or slugging, adding a lubricant and disintegrant and pressing into tablets. A powder mixture is prepared by mixing the compositions of the present invention, suitable comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The active ingredients can also be combined with free flowing inert carriers and compressed into tablets directly without going through the granulating or slugging steps. A protective coating consisting of a sealing coat of shellac, a coating of sugar or polymeric material and a polish coating of wax can be provided. Dye stuffs or pigments may be added to the tablets, for example, for identification or in order to characterize combinations of active doses. In tablet form the carrier comprises from about 0.1% to 99.9% by weight of the total composition.

The following examples are provided for illustrative purposes only. They are not intended, and should not be interpreted, to limit the scope of the invention which is more fully set forth in the claims which follow thereafter.

EXAMPLE 1

In Vitro Assay of Biological Activity of Astaxanthin.

Haemotococcus algae meal containing astaxanthin was assayed for 5α-reductase inhibitory activity in the form of a simulated digestion and absorption model, the preparation of which is described in USP volume 23. *Haematococcus pluvialis* algae meal (Cyanotech Corp., Kailua-Kona Hi.) was added to simulated gastric fluid which contained the gastric enzyme pepsin, thus simulating the digestive environment of the stomach. The contents were then shaken for dissolution of the test material. Following this incubation, the pH of the resulting mixture was then adjusted to approximately 7.4 by the addition of a 2.2N solution of sodium hydroxide and the addition of an equal volume of 2×concentrate of simulated intestinal fluid containing pancreatin. The flask was shaken at 250 RPM at 37° C. for 2 hours. This resulting solution was an approximation of physiologic intestinal fluid containing pancreatic enzymes that the test material would be exposed to upon oral consumption. The material was then flash frozen and stored at 80° C. for further testing.

Simulation of these physiological processes adds stringency to the assessment and indication of potential in vivo activity. As noted above, in a preferred embodiment of this invention, the astaxanthin administered in the methods of the invention is derived from *Haemotococcus pluvialis* microalgae. However, because herbs and natural extracts are complex materials, digestion may enhance or reduce absorption and subsequent biological activity.

The composition of the *Haemotococcus pluvialis* algae meal used in the examples was assayed and determined to have, by weight, 1.5 to 2% astaxanthin, 24% protein, 38% carbohydrate, 14% fatty acids, 14% ash, and 6–9% moisture. Table 1 shows the protein, fatty acid, mineral and vitamin content of the algae meal composition.

TABLE 1

ASTAXANTHIN POWDER

| PROTEIN | % | FATTY ACIDS | % | MINERALS | % |
|---|---|---|---|---|---|
| Tryptophan | 0.31 | Tetradecanoic (Myristic) | 0.07 | Calcium | 1.58 |
| Aspartic Acid | 1.89 | Hexadecanoic (Palmitic) | 3.82 | Magnesium | 1.14 |
| Threonine | 1.04 | Hexadecanoic (Palmitoleic) | 0.08 | Iron | 0.73 |
| Serine | 0.94 | Heptadecanoic (Margaric) | 0.03 | | |
| Glutamic Acid | 2.19 | Heptadecanoic (Margaroleic) | 0.17 | | |
| Proline | 0.89 | Octadecanoic (Stearic) | 0.27 | | |
| Glycine | 1.17 | Octadecanoic (Oleic) | 3.41 | | |
| Alanine | 1.73 | Octadecadienoic (Linolenic) | 2.74 | VITAMINS (mg/lb) | |
| Cystine | 0.19 | Octadecatrienoic (Linolenic) | 0.97 | Biotin | 0.337 |
| Valine | 1.36 | Gamma Linolenic-Omega 6 | 0.21 | Folic Acid | 1.30 |
| Methionine | 0.40 | Octadecatraenoic | 0.19 | Niacin (Nicotinic Acid) | 29.8 |
| Isoleucine | 0.79 | Eicosanoic (Arachidic) | 0.08 | Pantothenic Acid | 6.14 |
| Leucine | 1.67 | Eicosenoic (Gadoleic) | 0.04 | Vitamin B1 (Thiamine | 2.17 |

TABLE 1-continued

ASTAXANTHIN POWDER

| PROTEIN | % | FATTY ACIDS | % | MINERALS | % |
|---|---|---|---|---|---|
| | | | | Hydrochloride) | |
| Tryosine | 0.52 | Eicosadienoic | 0.16 | Vitamin B2 (Riboflavin) | 7.67 |
| Phenylalanine | 0.90 | Eicosatrienoic Gamma | 0.06 | Vitamin B6 | 1.63 |
| Histidine | 0.61 | Eicosatetraenoic (Arachidionic) | 0.18 | Vitamin B12 | 0.55 |
| Lysine | 1.13 | Eicosapentaenoic-Omega 3 (EPA) | 0.08 | Vitamin C (Ascorbic Acid) | 38.9 |
| Arginine | 1.07 | Docosanoic (Behemic) | 0.05 | Vitamin E | 186.1 IU/lb |
| | | Tetracosanoic (Lignoceric) | 0.03 | | |

Compositions can be tested for their ability to inhibit activity of 5α-reductase according to the bioassays disclosed in Delos, S. et al., *Journal of Steroid Biochemistry and Molecular Biology*, Vol. 48, pp. 347–352 (1994); and Iehle, C. et al., *Journal of Steroid Biochemistry and Molecular Biology*, Vol. 54, pp. 273–279 (1995), the contents of which are hereby incorporated into this specification in their entirety.

Further, a single multi-site assay is capable of modeling, in vitro, synergistic activity between inhibition of DHT formation and inhibition of DHT transformation of androgen receptor. The following mixture was used to assay for biological activity: recombinant 5α-reductase or microsomes containing 5α-reductase, cofactor NADPH, substrate testosterone in limiting concentration, cytosol or nuclear extract containing competent unliganded androgen receptor bound to HSP90, and biotinylated androgen response element DNA in limiting concentration. Aliquots of the mixture are challenged with a sample of the test compound (LESP and/or Haemotococcus algae meal containing astaxanthin), a positive control comprising a similarly prepared sample lacking the test compound, and a negative control lacking both testosterone and the test compound. The assay detects the inhibition of the formation of DHT from testosterone which is catalyzed by 5α-reductase. DHT binds to and transforms androgen receptor, such that androgen receptor can bind to androgen response element DNA. Thus, by inhibiting the formation of DHT, the test compound is determined to inhibit the transformation of androgen receptor into the form which is capable of binding to androgen response element DNA.

To detect whether androgen receptor has been transformed, the mixture is contacted with neutravidin, avidin, or streptavidin bound to an ELISA plate, whereby the biotinylated androgen response element DNA of the mixture is immobilized. Androgen receptor in the mixture, if transformed by DHT, forms a complex with the androgen response element DNA and is thus immobilized. Unbound materials are washed away. The ELISA plate is contacted with anti-androgen receptor antibody, such that the antibody binds to the androgen response element-androgen receptor complex on the plate. The antibody and complex is detected using a fluorescent tag or other detectable moiety such as a second antibody coupled to alkaline phosphatase enzyme. Alkaline phosphatase is detected enzymatically using para nitrophenyl phosphate (PNPP) and measured calorimetrically in an ELISA plate reader. The activity of the sample less the negative control divided by positive control less the negative control gives percent inhibition of the test compound.

The data in Tables 2 and 3 below demonstrate that Haemotococcus algae meal containing astaxanthin alone and in combination with LESP inhibits the activity of 5α-reductase after simulated digestion and inactivation of intestinal enzymes by boiling or heating.

TABLE 2

| Product/Extract Tested (50 ug/mL) | Percent 5α-Reductase Inhibition | Standard Deviation |
|---|---|---|
| Placebo | 1.2% | 1% |
| Control 1 | 50% | 4.7% |
| Control 2 | 41% | 3.1% |
| Sample 1 | 43% | 1.7% |
| Sample 2 | 43% | 1.4% |
| Sample 3 | 42% | 1.8% |

Table 2 shows the results of inhibition assays on a placebo (containing only oil and no saw palmetto or algae meal containing astaxanthin), and two controls: (1) a hexane extract of saw palmetto and (2, an ethanol extract of saw palmetto. These were compared with three samples comprising mostly LESP and varying weight percentages of algae meal containing astaxanthin. Sample 1 contained 10% algae meal, Sample 2 contained 5% algae meal and Sample 3 contained 2.5% algae meal.

TABLE 3

| Product/Extract Tested (50 ug/mL) | Percent 5α-Reductase Inhibition | Standard Deviation |
|---|---|---|
| Placebo | 1.1% | 1.0% |
| Control 1 | 49% | 2.9% |
| Control 2 | 35% | 2.8% |
| Sample 4 | 34% | 2.7% |
| Sample 5 | 34% | 2.3% |
| Sample 6 | 98% | 2.0% |

Table 3 shows the results of inhibition assays of the two controls and placebo referred to in Table 2 above and three additional samples. Sample 4 containing LESP and 1% by weight algae meal containing astaxanthin, sample 5 containing LESP and 0.5% by weight algae meal, and sample 6 containing only algae meal (300 μg/mL) and no LESP. As seen in Table 3, by itself, the algae meal containing astaxanthin showed an inhibition of 5α-reductase of 98%.

EXAMPLE 2

Human Prostate Cancer Cellular Proliferation Assay.

The NOVASCREEN cellular proliferation assay employs the use of a proprietary green fluorescent dye, CyQuant®GR (Molecular Probes) which shows strong fluorescent enhancement when bound to cellular nucleic acids. Since cell proliferation is always accompanied by an increase in the absolute amount of nucleic acid, this method, similar to established procedures like $^3$H thymidine incorporation, can be used to quantify the amount of cell division. Unlike conventional methods, the use of this fluorescent dye enables stable associations with nucleic acids which allow for cells to be frozen and stored so treatments over several days can be assayed together to reduce experimental variation.

Cell Growth and Plating

LNCaP-FGC (human prostatic cancer cells) are grown for four days at 37° C. and 5% $CO_2$ to confluence in RPMI 1640+2 mM 1-glutamine+10% fetal Bovine Serum (FBS)+

4.5g/L glucose+10% HEPES+1 mM Sodium Pyruvate in a T175 flask (Costar). Cells are harvested by trypsinization and are then centrifuged at 600×g and resuspended to a concentration of 4×10³ cells/ml. Cells are checked for >95% viability and then plated out in six 96 well plates (Costar) at a density of 2000 cells per well in 200 µl of RPMI 1640+2 mM 1-glutamine +10% fetal Bovine Serum (FBS)+4.5g/L glucose+10% HEPES+1 mM Sodium Pyruvate (growth medium).

Cell Treatment

Six plates were seeded at 2000 cells/well. One plate was removed, washed and frozen to serve as a baseline on the same day as the chemical treatment. Media was aspirated from five plates and then treated with chemicals diluted in growth medium. Cell proliferation was followed for 1 week. Vancomycin was prepared at $1\times10^{-3}$ M, diluted to a final concentration of $1\times10^{-4}$, $10^{-5}$, $10^{-6}$, $10^{-7}$, $10^{-8}$, $10^{-9}$M in the wells. Saw Palmetto lipid extract and Haemotococcus algae meal containing astaxanthin at 2.5% and 5.0% wt/wt (dissolved in saw palmetto lipid extract) was prepared and diluted to a final dilution of 1:10, 1:100, 1:1000, 1:10,000, 1:100,000 and 1:1,000,000. All plates were then returned to a humidified incubator at 37° C. and 5% $CO_2$ to continue growth. Plates were removed from the incubator on days 1, 2, 7, 8 and 9. The plates were then washed and frozen at −70° C. until assayed.

Proliferation Assay

The 6 plates (including the baseline plate) were removed from the −70° C. freezer and allowed to reach room temperature. In subdued light, the CyQuant GR dye (Molecular Probes) was prepared. The Cell Lysis Buffer stock solution was diluted 20-fold in distilled water. For each well assayed, 100 µl of buffer was required Just prior to the assay, the CyQuant GR stock solution was diluted 800-fold into 1× Lysis Buffer.

For each 96 well plate:

Cell Lysis Buffer: 500 µl 20× stock+1.5 ml distilled water.
CyQuant-GR Reagent: 10 ml Lysls Buffer+12.5 µl
CyQuant Stock Solution.

The CyQuant-GR Reagent should be prepared in a plastic container that is protected from light. 100 µl of the CyQuant-GR Reagent was added to each well, agitated and allowed to incubate for 10 min at room temperature in the dark. The fluorescence was quantified on a Victor2 fluorometer with an excitation wavelength of 485 nm and an emission wavelength of 535 nm. All test compound data were reported as percent of total control wells on the same plate. A standard curve of bacteriophage Λ phage DNA was performed on a separate plate in duplicate on the day of the assay. Table 4 shows the results of the assays of the various concentrations of the algae meal composition containing astaxanthin. As a comparison Table 5 shows the results of the assays using LESP. As seen below, the algae meal composition containing astaxanthin shows inhibition of prostate cancer cell growth comparable to the levels shown for LESP but at a lower concentration.

TABLE 4

% Inhibition of Untreated Cells

| Day | $10^{-9}$ | $10^{-8}$ | $10^{-7}$ | $10^{-6}$ | $10^{-5}$ | $10^{-4}$ |
|---|---|---|---|---|---|---|
| 0 | −12 | −5 | 4 | 5 | −1 | −3 |
| 1 | −5 | −4 | 4 | −4 | 11 | 27 |
| 2 | −4 | −1 | −3 | −5 | 20 | 22 |
| 7 | 4 | −2 | −2 | −1 | 21 | 26 |
| 8 | −2 | 0 | −1 | −3 | 32 | 19 |
| 9 | −2 | −3 | −1 | −3 | 38 | 24 |

TABLE 5

% Inhibition of Untreated Cells

| Day | $10^{-9}$ | $10^{-8}$ | $10^{-7}$ | $10^{-6}$ | $10^{-5}$ | $10^{-4}$ |
|---|---|---|---|---|---|---|
| 0 | −8 | −8 | 1 | 0 | 8 | −1 |
| 1 | 0 | −1 | 6 | −8 | −6 | 34 |
| 2 | −9 | 9 | 2 | 2 | −6 | 28 |
| 7 | −8 | −2 | 0 | −1 | −7 | 48 |
| 8 | −5 | 1 | −4 | −4 | −3 | 42 |
| 9 | −7 | −2 | −5 | −8 | −9 | 34 |

What is claimed is:

1. A method for inhibiting the activity of the enzyme 5-α-reductase in a human subject which comprises administering to the subject a composition comprising (a) from about 15% and about 35% by weight protein, (b) from about 15% to about 60% by weight carbohydrates, (c) from about 1% to about 30% by weight fatty acids, and (d) from about 0.1% to about 4.0% by weight of the carotenoid astaxanthin.

2. The method of claim 1 wherein the composition is derived from *Haematococcus pluvialis* algae meal.

3. The method of claim 1 wherein the composition further comprises saw palmetto extract.

4. A method for treating benign prostate hyperplasia (BPH) in a subject in need thereof which comprises administering to the subject a composition comprising (a) from about 15% to about 35% by weight protein, (b) from about 15% to about 60% by weight carbohydrates, (c) from about 1% to about 30% by weight fatty acids, and (d) from about 0.1% to about 4.0% by weight of the carotenoid astaxanthin.

5. The method of claim 4 wherein the composition is derived from *Haematococcus pluvialis* algae meal.

6. The method of claim 4 wherein the composition further comprises saw palmetto extract.

7. A method for treating prostate cancer in a subject in need thereof which comprises administering to the subject a composition comprising (a) from about 15% to about 35% by weight protein, (b) from about 15% to about 60% by weight carbohydrates, (c) from about 1% to about 30% by weight fatty acids, and (d) from about 0.1% to about 4.0% by weight of the carotenoid astaxanthin.

8. The method of claim 7 wherein the composition is derived from *Haematococcus pluvialis* algae meal.

9. The method of claim 7 wherein the composition further comprises saw palmetto extract.

* * * * *